US00PP25988P2

(12) United States Plant Patent
Ault

(10) Patent No.: US PP25,988 P2
(45) Date of Patent: Oct. 13, 2015

(54) ***TRADESCANTIA* PLANT NAMED 'TOUGH LOVE'**

(50) Latin Name: ***Tradescantia* hybrid**
Varietal Denomination: Tough Love

(71) Applicant: James R. Ault, Libertyville, IL (US)

(72) Inventor: James R. Ault, Libertyville, IL (US)

(73) Assignee: CHICAGOLAND GROWS, INC., Glencoe, IL (US)

( * ) Notice: Subject to any disclaimer, the term of this patent is extended or adjusted under 35 U.S.C. 154(b) by 114 days.

(21) Appl. No.: 13/999,270

(22) Filed: Feb. 5, 2014

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Penny J. Aguirre

(57) ABSTRACT

A new hybrid cultivar of *Tradescantia*, 'Tough Love' that is characterized by its very compact plant habit reaching an average of 23 cm in height after two years of growth, its leaves that are held upright to horizontal and straight to arching in aspect, its foliage that is very strong, leathery in texture, and pubescent along the margins and on both surfaces, its pedicels, flower buds, and leaves that are densely pubescent, its flowers that are vivid red-purple in color, its drought tolerance remaining evergreen throughout the summer, and its resistance to rust.

2 Drawing Sheets

Genus and species: *Tradescantia* hybrid.
Cultivar: 'Tough Love'.

BACKGROUND OF THE INVENTION

The present invention, *Tradescantia* 'Tough Love', relates to a new and distinct interspecific hybrid of *Tradescantia*, hereinafter referred to by its cultivar name, 'Tough Love'. 'Tough Love' represents a new hybrid spiderwort, a herbaceous perennial grown for landscape use.

The new cultivar was derived from a controlled breeding program conducted by the Inventor at Chicago Botanic Garden in Chicago, Ill., USA. 'Tough Love' arose from a cross made in May of 2009 between an unnamed open pollinated seedling of *Tradescantia tharpii* as the female parent and an unnamed plant of *Tradescantia occidentalis* as the male parent. 'Tough Love' was selected as a single unique plant in June of 2009 from amongst the seedlings derived from the above cross.

Asexual propagation of the new cultivar was first accomplished by the Inventor by division of dormant rootstock in Glencoe, Ill. in April of 2010. Asexual propagation by division of dormant rootstock has determined that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Tough Love' as a new and unique cultivar of *Tradescantia*.

1. 'Tough Love' exhibits a very compact plant habit, reaching an average of 23 cm in height after two years of growth.
2. 'Tough Love' exhibits leaves that are held upright to horizontal and straight to arching in aspect.

3. 'Tough Love' exhibits foliage that is very strong, leathery in texture, and very pubescent along the margins and on both surfaces.
4. 'Tough Love' exhibits pedicels, flower buds, and leaves that are densely pubescent.
5. 'Tough Love' exhibits flowers that vivid red-purple in color.
6. 'Tough Love' exhibits good drought tolerance and does not go dormant in the summer (summer dormancy is typical of most cultivars of *Tradescantia*. known to the Inventor).
7. 'Tough Love' exhibits good resistance to rust.

The female parent of 'Tough Love', an unnamed open pollinated seedling of *Tradescantia tharpii*, differs from 'Tough Love' in having flowers that are dark purple in color, in being taller in height (average of 34 cm), and in having flowers that are larger in diameter. The male parent of 'Tough Love', an unnamed plant of *Tradescantia occidentalis*, differs from 'Tough Love' in being taller in height, in having pedicels and sepals that are sparsely pubescent, and in having foliage that is weaker, held strongly pendulous, and pubescent only along the leaf margins. 'Tough Love' can be most closely compared to the *Tradescantia* cultivars, 'Concord Grape' (not patented) and 'Blue and Gold' (not patented). Both cultivars are similar to 'Tough Love' in having good resistance to rust and in blooming from mid-May into September. 'Concord Grape' differs from 'Tough Love' in being taller in height (average of 60 cm), in having flowers that are purple in color, and in having glabrous pedicels and sepals. 'Blue and Gold' differs from 'Tough Love' in being taller in height (average of 40 cm), in having flowers that are purple-blue in color, in having glabrous pedicels and sepals, and in having foliage that is golden yellow in color.

BRIEF DESCRIPTION OF THE DRAWINGS

The accompanying colored photographs illustrate the overall appearance and distinct characteristics of the new *Trades-*

*cantia*, 'Tough Love'. The photographs were taken of plants of 'Tough Love' as grown outdoors in the ground in Glencoe, Ill.

Figure 1:
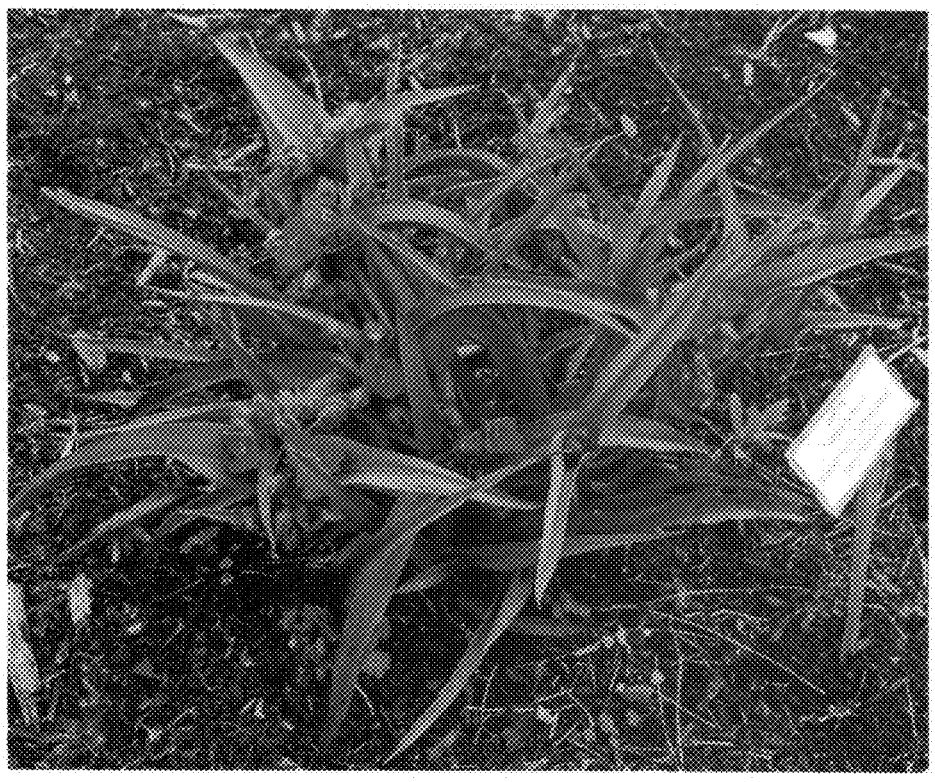

The photograph in FIG. 1 provides an overall view of the plant habit of a three year-old plant of 'Tough Love'.

Figure 2:
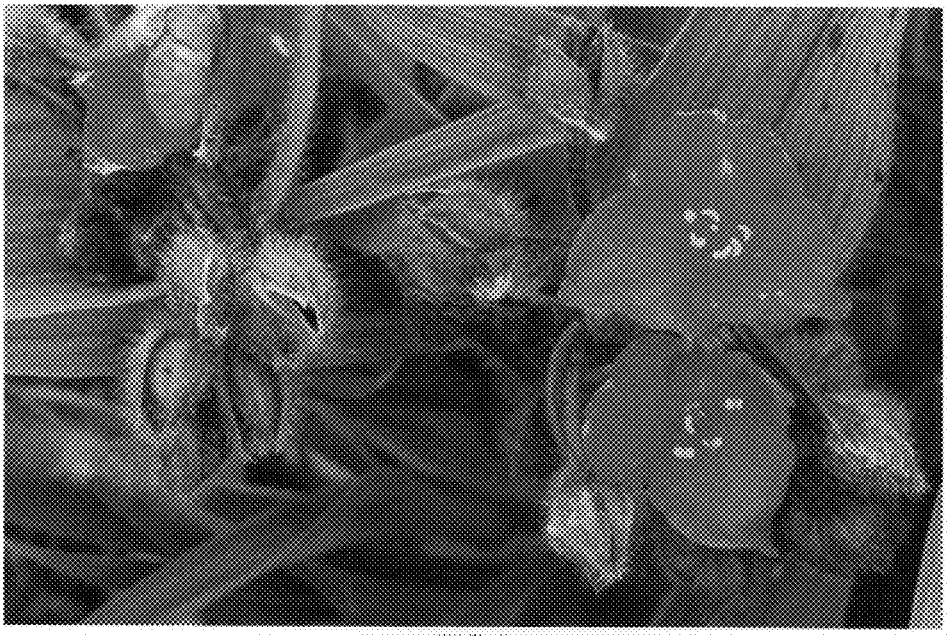

The photograph in FIG. 2 provides a close-up view of the inflorescences and dense flower bud pubescence of a three year-old plant of 'Tough Love'.

Figure 3:
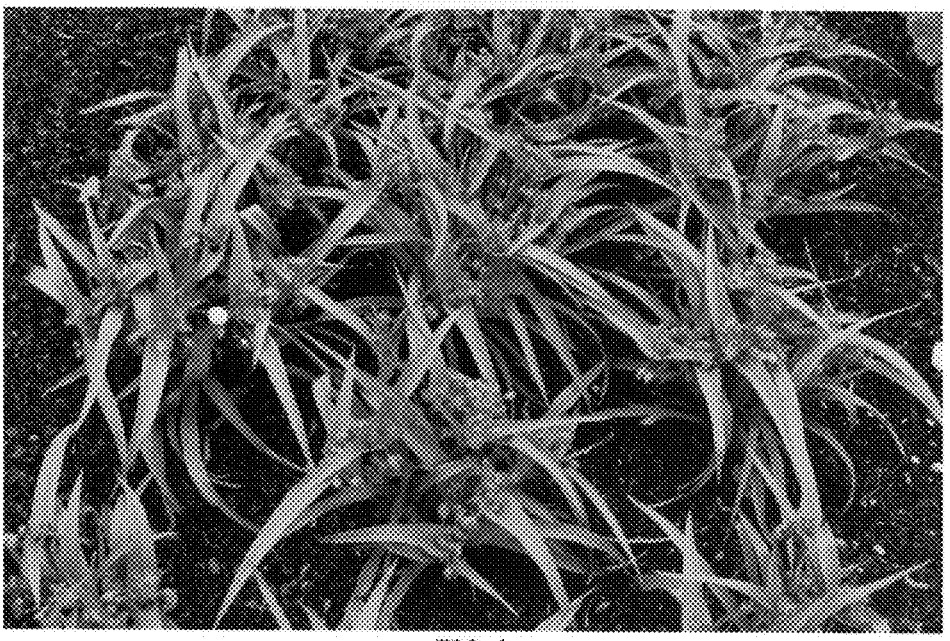

The photograph of FIG. 3 provides an overall view of one-year old plants grown from dormant root division of 'Tough Love'.

The colors in the photographs are as close as possible with the photographic and printing technology utilized and the color values cited in the Detailed Botanical Description accurately describe the colors of the new *Tradescantia*.

BOTANICAL DESCRIPTION OF THE PLANT

The following is a detailed description of one year-old plants of the new cultivar as grown in a 4-inch container in Glencoe, Ill. with mature plant size taken from plants three years in age as grown outdoors in a trial garden in Glencoe, Ill. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Mid May into September in northern Illinois.

*Plant type*.—Herbaceous perennial.

*Plant habit*.—Clump-forming and compact.

*Height and spread*.—An average of 23 cm in height and 38 cm spread.

*Cold hardiness*.—At least to U.S.D.A. Zones 4 to 8.

*Diseases and pests*.—Good resistance to rust has been observed.

*Root description*.—Rhizomes with attached fine and fibrous roots.

*Propagation*.—Division of dormant rootstock.

*Growth rate*.—Moderate.

Stem description:

*Shape*.—Round.

*Stem color*.—Young stems; 145C, mature stem; a blend of 187A and 137B.

*Stem size*.—Main stems; 5 mm in diameter and 15 cm in length, Side branches; 7 cm in length and 5 mm in diameter as grown in a 4 inch pot.

*Stem surface*.—Young stem; glabrous, moderately covered with long fine white hairs about 2 mm in length and NN155D in color, mature stem; glabrous, very sparsely covered with fine white hairs, 1 mm in length and NN155D in color.

*Branching*.—3 primary branches on a 4-inch pot, 1 to 2 secondary branches.

*Internode length*.—Up to 6 cm.

Foliage description:

*Leaf shape*.—Lanceolate.

*Leaf division*.—Simple.

*Leaf base*.—Cordate, clasping around entire stem, appears perfoliated.

*Leaf apex*.—Acute.

*Leaf venation*.—Camptodrome, almost parallel, typically 7 pairs of veins surrounding midrib. Slightly recessed on upper and lower surface, color matching the color of foliage on lower surface and distal portion of upper surface, color is N137A on basal portion of upper surface.

*Leaf margins*.—Entire.

*Leaf attachment*.—Clasping, appearing perfoliated, no petiole.

*Leaf arrangement*.—Alternate.

*Leaf substance*.—Strong and leathery.

*Leaf surface*.—Upper; scabrous pubescence, imparting a slight silver cast, lower; scabrous but smoother than the upper surface and covered with sparse long white hairs towards the base up to 2 mm in length and NN155D in color.

*Leaf color*.—Newly formed leaves, upper and lower surface: between 144A and 144B, mature leaves, upper and lower surface; 147B, leaf color is retained throughout the summer (no summer dormancy).

*Leaf size*.—Up to about 18 cm in length, 1 cm in width.

*Leaf quantity*.—Up to about 11 per stem with two secondary branches.

*Foliage aspect*.—Held upright to horizontal and straight to arching in aspect.

Flower description:

*Inflorescence type*.—Umbel-like cyme at terminal leaf nodes.

*Lastingness of inflorescence*.—Individual blooms last about one day, inflorescence blooms for about 4 weeks.

*Inflorescence size*.—About 6 cm in width and 5 cm in depth with 2-3 flowers open.

*Flower fragrance*.—None.

*Flower buds*.—Ovate in shape, 1.3 cm in length and 1 cm in width, color is a blend of N77A, N77B and 138A, surface is pubescent with hairs about 1 mm in length.

*Perianth form*.—Open bell-shaped, comprised of 3 fused tepals having a saccate base.

*Flower aspect*.—Held upward on upper surface of cascading stems, tepal tips are reflexed.

*Flower size*.—About 1 cm in depth, about 3 cm in width.

*Flower number*.—Up to 14 per stem, about 20 blooms on a 4-inch potted plant with 3 main stems.

*Petal color*.—(Opening and mature), upper and lower surface; N78A with a slight blend of 72B.

*Petal surface/appearance*.—Upper and lower surface are glabrous.

*Petal size*.—Average of 1.5 cm in length and 1.5 in width.

*Petal apex*.—Bluntly acute.

*Petal base*.—Truncate.

*Petal base*.—Entire.

*Sepals*.—3, 1 cm in length, 5 mm in width, ovate in shape, acute apex, entire margin, cup shaped, outer surface slightly sheen appearance and covered with long white hairs 3 mm in length and NN155D in color, color; 145A becoming 145D at the margins, inner surface glabrous and glossy, color; tip 145B blending towards the base becoming 137A in color with margins becoming 145D.

*Peduncles*.—None.

*Pedicels*.—Arise from leaf node at center of leaf attachment, about 2 cm in length, about 1 mm in width, 139A at the base blending up towards the top with N79A, sparsely covered with long wooly white hairs 2 mm in length and NN155D in color.

Reproductive organs:

*Gynoecium*.—Pistil; 1, 5 mm in length and 1 mm in width, style is 4 mm in length and 1 mm in width and 77A in color, stigma is club shaped, flattened 91D in color, ovary is 1 mm in length and 2 mm in width, 158A in color.

*Androcoecium*.—6 stamens; anther attachment is basifixed, orbicular in shape and flattened, 1 mm in length and width, 14A in color, filament is 4 mm in length and 77A in color, filament hairs are at the base of each filament, average of 30 fine wavy hairs up to 3 mm in length and 77A in color, pollen is low in quantity and 14A in color.

*Fruit and seeds*.—Not observed.

It is claimed:

1. A new and distinct cultivar of a *Tradescantia* hybrid plant named 'Tough Love' substantially as herein illustrated and described.

* * * * *